United States Patent [19]

Chodnekar

[11] 4,005,216
[45] Jan. 25, 1977

[54] PHENYL CARBAMATE

[75] Inventor: Madhukar Subraya Chodnekar, Seltisberg, Switzerland

[73] Assignee: Hoffmann-La Roche Inc., Nutley, N.J.

[22] Filed: Feb. 12, 1976

[21] Appl. No.: 657,507

[30] Foreign Application Priority Data

Mar. 7, 1975 Switzerland .................... 2905/75

[52] U.S. Cl. ............................ 424/282; 260/340.5
[51] Int. Cl.² ........................................ A61K 31/36
[58] Field of Search ................ 260/340.5; 424/282

[56] References Cited

UNITED STATES PATENTS

| | | | |
|---|---|---|---|
| 3,509,200 | 4/1970 | Elpern et al. | 260/340.5 X |
| 3,663,594 | 5/1972 | Brown et al. | 260/470 |
| 3,781,331 | 12/1973 | Kühle et al. | 260/479 |
| 3,829,437 | 8/1974 | Zumach | 260/340.7 X |

*Primary Examiner*—Ethel G. Love
*Attorney, Agent, or Firm*—Samuel L. Welt; Bernard S. Leon; William H. Epstein

[57] ABSTRACT

The compound 2,3-(isopropylidenedioxy) phenylmethyl [(trichloromethyl)-thio]-carbamate and its use as an insecticide and insecticidal compositions containing same compound.

4 Claims, No Drawings

PHENYL CARBAMATE

BACKGROUND OF INVENTION

Phenyl carbamates have been known as insecticides. See German DOS No. 1,910,259, British Pat. No. 1,220,056, German DOS No. 2,341,949, German DOS No. 1,922,929, German DOS No. 2,311,384 and Pesticide Science, 1972, 3, pg. 735–744. However, there is no disclosure of these publications of a phenyl carbamate containing isopropylidene group and trichloromethyl thio substituent.

SUMMARY OF THE INVENTION

The phenylcarbamate provided by the present invention is 2,3-(isopropylidenedioxy)phenyl-methyl[(trichloromethyl)-thio]carbamate of the formula:

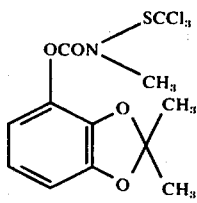

(I)

The phenylcarbamate of formula I is useful as an agent for the control of pests and is especially suitable for the control of insects such as flies, caterpillars, beetles, aphids and Hemiptera.

DETAILED DESCRIPTION

According to the process provided by the present invention, the phenylcarbamate of formula I is manufactured by reacting 2,2-dimethyl-4-hydroxy-1,3-benzodioxol of the formula:

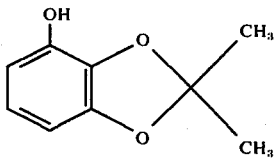

II with a compound of the general formula

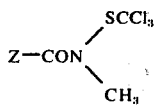

III

, wherein Z represents a chlorine, bromine or iodine atom,
in the presence of a base, As used in this specification, the term "halogen" includes chlorine, bromine and iodine.

According to a preferred embodiment of the present process, the reaction of 2,2-dimethyl-4-hydroxy-1,3-benzodioxol of formula II with a compound of formula III is carried out according to methods known per se; conveniently in the presence of an excess of the compound of formula III. The reaction is conveniently carried out in an inert organic solvent such as a hydrocarbon (e.g. benzene or toluene), a chlorinated hydrocarbon (e.g. methylene chloride), an ether (e.g. diethyl ether) and the like. Examples of bases which can be used as a catalyst are potassium carbonate, sodium carbonate, triethylamine, pyridine and the like. The temperature and pressure are not critical and it is preferred to carry out the reaction at a temperature between about 0° C and the reflux temperature of the reaction mixture, preferably at a temperature between room temperature and 130° C.

The starting materials used in the process provided by the present invention are known.

As mentioned earlier, the present invention is also concerned with pesticidal compositions which contain the phenylcarbamate of formula I as the essential active ingredient in association with a compatible carrier material. These pesticidal compositions conveniently contain at least one of the following materials: carrier substances, wetting agents, inert diluents and solvents.

The present invention is also concerned with a method for providing a locus subject to or subjected to attack by pests free from such attack, which method comprises applying to said locus an effective amount of a pesticidal composition, as hereinbefore defined, or of the phenylcarbamate of formula I. Thus, for example, the present pesticidal compositions or the phenylcarbamate of formula I can be used for the control of pests on plants and animals and in the soil as well as on objects and areas.

It will be evident from the foregoing that the phenylcarbamate of formula I is quite generally of value as a pesticide. It is especially valuable as an insecticide, especially against flies, caterpillars, beetles, aphids and Hemiptera. Examples of species are:

Aedes aegypti
Ceratitis capitata
Culex pipiens
Musca domestica
Calliphora sp.
Adoxophyes reticulana
Heliothis virescens
Laspeyresia pomonella
Mamestra brassicae
Ostrinia nubilalis
Plodia interpunctella
Plutella xylostella
Aphis fabae
Aphis pomi
Megoura viciae
Macrosiphum euphorbiae
Aonidiella aurantii
Quadraspidiotus perniciosus
Laodelphax striatellus
Nephotettix virescens
Saissetia coffeae
Saissetia oleae
Myzus persicae
Planococcus citri
Dysaphis plantaginea
Dysdercus cingulatus
Dermestes maculatus
Epilachna chrysomelina
Leptinotarsa decemlineata
Oryzaephilus surinamensis
Otiorhynchus sulcatus
Rhizopertha dominica
Sitophilus granarius
Tenebrio molitor
Tribolium castaneum Blattella germanica
Blatta orientalis
Periplaneta americana
Ditylenchus dipscaci The present phenylcarbamate acts as a direct insecticide and, to some extent, also has systemic activity. The phenylcarbamate of formula I is also of value for the control of pests on animals. Thus, for example, the phenylcarbamate of formula I has an activity of 100% in a concentration of $10^{-6}$ g/cm$^2$ in the test against Aphis fabae. The acute oral toxicity of the phenylcarbamate of formula I in the rat amounts to more than 5000 mg/kg.

The phenylcarbamate of formula I is insoluble in water and can be made up into a form ready-for-use according to any of the methods which are customary for insoluble compounds.

If desired, the phenylcarbamate of formula I can be dissolved in water-immiscible solvent, such as, for example a high-boiling hydrocarbon, which conveniently contains dissolved emulsifiers, so that it acts as a self-emulsifiable oil upon addition to water.

The phenylcarbamate of formula I can also be mixed with a wetting agent, with or without inert diluent, for the formation of a wettable powder which is soluble or dispersible in water, or it can be mixed with an inert diluent for the formation of a solid or pulverous product.

Inert diluents with which the phenylcarbamate of formula I can be compounded are solid inert media, including pulverous or finely divided solid materials such as, for example, clays, sands, talc, mica, fertilizers and the like, such materials being present either in the form of dusts or as materials being present either in the form of dusts or as materials having a larger particle size.

The wetting agent can be an anionic wetting agent such as, for example, soaps, fatty sulfate esters such as dodecyl sodium sulfate, octadecyl sodium sulfate and cetyl sodium sulfate, fatty-aromatic sulfonates such as alkylbenzene sulfonates or butylnaphthalene sulfonates, complex fatty sulfonates such as the amide condensation product of oleic acid and N-methyltaurine or the sodium sulfonate of dioctyl succinate.

The wetting agent can also be a non-ionic wetting agent such as, for example, condensation products of fatty acids, fatty alcohols or fat-substituted phenols with ethylene oxide, or fatty acid esters and ethers of sugars or polyvalent alcohols or the products which are obtained from the latter by condensation with ethylene oxide, or the products which are known as block co-polymers of ethylene oxide and propylene oxide.

The wetting agent can also be a cationic agent such as, for example, cetyltrimethylammonium bromide and the like.

The present pesticidal compositions can also be made up in the form of an aerosol, there being conveniently present in addition to the propellant gas, which is suitably a polyhalogenated alkane such as dichlorodifluoromethane, a co-solvent and a wetting agent.

The pesticidal compositions provided by the present invention can contain, in addition to the phenylcarbamate of formula I, other active insecticides, bactericides and fungicides.

In its various applications as an agent for the control of pests, the phenylcarbamate of formula I can be used in different ratios. Thus, for example, for the control of pests on plants, the phenylcarbamate of formula I is conveniently used in an amount of about 10–1000 g/ha.

The following Examples illustrate the present invention. Example 1 illustrates the process and Example 2 illustrates a pesticidal composition:

EXAMPLE 1

5g of sodium hydride (50% by weight dipersion in oil) are washed out twice with petroleum ether having a boiling point of 35° to 45° C and then suspended in 75 ml of absolute benzene in a four-necked round-bottomed flask. 16.6g (0.1 mol) of 2,3-(isopropylidenedioxy)phenol are added portionwise thereto while stirring and the resulting mixture is stirred for 30 minutes at room temperature. Thereafter, 26.7 g of N-trichloromethylthio-N-methylcarbamic acid chloride (freshyl prepared) are added dropwise over a period of 1 hour in benzolic solution (20 ml of benzene). The mixture is subsequently further stirred at room temperature for 4 hours under an atmosphere of nitrogen as the protecting gas. The mixture is poured on to 200 ml of ice-water and extracted three times with benzene. The benzene extract is washed twice with water, dried over sodium sulfate, filtered and evaporated. There is obtained 2,3-(isopropylidenedioxy)phenyl-methyl[(trichloromethyl)thio]carbamate in the form of yellow crystals of melting point 88°–89° C after recrystallization from high-boiling petroleum ether.

EXAMPLE 2

A sprayable powder containing the following ingredients is manufactured:
50% by weight phenylcarbamate of formula I,
5% by weight high-dispersible silicic acid,
1% by weight sodium lauryl sulfate,
2% by weight sodium lignosulfonate (sulfate cellulose spent liquor) and
42% by weight kaolin.

The foregoing components are mixed and finely ground in a suitable mill. In order to prepare a ready-to-spray solution, the powder is stirred into the desired amount of water.

I claim:

1. 2,3-(Isopropylidenedioxy)phenyl-methyl[(trichloromethyl)thio]carbamate of the formula:

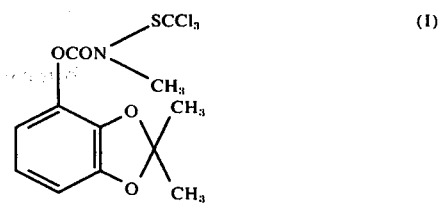

2. A composition effective against flies, caterpillars, bettles, aphids and Hemiptera comprising an insecticidal effective amount of the compound 2,3-(isopropylidenedioxy)phenyl-methyl[(trichloromethyl)thio]carbamate and a compatible inert carrier.

3. A method for providing a locus subject to or subjected to attack by insects selected from the group consisting of flies, caterpillars, beetles, aphids, and Hemiptera free from such attack comprising applying to said locus an insecticidal effective amount of 2,3-(isopropylidenedioxy)phenyl-methyl[(trichloromethyl)thio]carbamate.

4. The method of claim 3 wherein said locus is a plant or animal.

* * * * *